United States Patent [19]

Ehmann

[11] 4,055,601

[45] Oct. 25, 1977

[54] PROCESS FOR THE OXIDATION OF PRIMARY ALLYLIC ALCOHOLS

[75] Inventor: William J. Ehmann, Orange Park, Fla.

[73] Assignee: SCM Corporation, New York, N.Y.

[21] Appl. No.: 582,114

[22] Filed: May 30, 1975

Related U.S. Application Data

[63] Continuation-in-part of Ser. No. 437,188, Jan. 28, 1974, abandoned.

[51] Int. Cl.² .............................................. C07C 45/16
[52] U.S. Cl. ............................ 260/593 R; 260/603 C; 260/347.8; 260/599; 260/600 R; 260/598
[58] Field of Search ............ 260/603 HF, 599, 603 C, 260/593 R, 600 R, 598

[56] References Cited

U.S. PATENT DOCUMENTS 2,801,266   7/1957   Schinz ........................... 260/603 HF

OTHER PUBLICATIONS

Djerassi, "Organic Reactions", vol. VI, chapt. 5, pp. 207–234.
Adkins, et al., "J. Amer. Chem. Soc." vol. 71, pp. 3622–3629.
Batty et al., "Chem. Society Journal" (1938), pp. 175–179.

*Primary Examiner*—Bernard Helfin
*Attorney, Agent, or Firm*—Richard H. Thomas

[57] ABSTRACT

Improved conversions of 3-substituted and 3,3-disubstituted allyl alcohols to the corresponding aldehydes are obtained in an Oppenauer oxidation process, under Oppenauer oxidation conditions, by carrying out the oxidation employing furfural as the hydrogen acceptor. The invention is particularly applicable to the oxidation of geraniol and nerol to citral, which can be converted directly to pseudoionone without purification.

13 Claims, No Drawings

4,055,601

PROCESS FOR THE OXIDATION OF PRIMARY ALLYLIC ALCOHOLS

This application is a continuation-in-part of prior application Ser. No. 437,188, filed Jan. 28, 1974, now abandoned and assigned to assignee of the present application.

BACKGROUND OF THE INVENTION

The present invention relates to the Oppenauer oxidation of primary allylic alcohols to their corresponding aldehydes. The invention is particularly applicable to the Oppenauer oxidation of 3-substituted and 3,3-disubstituted allyl alcohols, and will be described primarily with respect to the Oppenauer oxidation of geraniol (trans) and nerol (cis)(3,7-dimethyl-2,6-octadien-1-ol) to citral (3,7-dimethyl-2,6-octadienal), although it will be apparent to those skilled in the art that the present invention has other applications.

Citral which is a mixture of citral-a (geranial) and citral-b (neral) is a highly useful intermediate in the syntheses of several desirable products. The syntheses of ionones and methyl ionones begin with citral. It may be converted via a condensation with acetone, directly to pseudoionone, which in turn can be converted into α-ionone and β-ionone. The latter is a key intermediate in the production of Vitamin A. Pseudoionone is useful in the production of Vitamin E. Citral has many other uses, for instance, in synthetic flavors.

DESCRIPTION OF THE PRIOR ART

The Oppenauer oxidation of secondary alcohols to ketones is a useful and well-known textbook reaction. The oxidation is carried out generally in the presence of an aluminum catalyst such as aluminum tert-butoxide or aluminum isopropoxide employing a large excess of acetone as a hydrogen acceptor. The general application of this reaction is, however, for secondary alcohols. It is reported in "Organic Reactions", Vol. VI, chapter 5, on "The Oppenauer Oxidation", (pages 222-223) by Carl Djerassi John Wiley and Sons Inc., 1951; "Until very recently the Oppenauer reaction, except in isolated instances, has not been used as a preparative method for the oxidation of primary alcohols to aldehydes because the aldehydes condensed with the hydrogen acceptor." As indicated by Djerassi, experimental modifications in the usual Oppenauer procedure are necessary. These include the use of expensive or difficult to come by hydrogen acceptors, use of stoichiometric amounts of catalyst and careful distillation of the product as it is formed. The methods are expensive, difficult to carry out on a large scale and are employed only when no other method is available.

The Djerassi text in "Organic Reactions" is incorporated by reference herein.

Previous observations of the oxidation of geraniol and nerol with acetone as a hydrogen acceptor show that the aldehydes produced undergo a subsequent aldolcondensation reaction with the acetone and little aldehyde (citral) is actually recoverable. Although the end product of the aldol condensation of citral is pseudoionone, two major problems have kept this reaction from being employed in the production of psuedoionone commercially. One problem is that the aldol condensation reaction produces water as a by-product which hydrolyzes and consumes the aluminum catalyst. This requires nearly stoichiometric quantities (as compared to catalytic quantities) of the aluminum catalyst (notice page 224 of Djerassi, supra). In addition, the hydrolyzed catalyst is in the form of a gel-like precipitate which is difficult to dispose of and which also presents mechanical problems in carrying out the oxidation reaction. Still further, large amounts of solvent are required to dissolve the correspondingly large amount of catalyst employed for the oxidation reaction. A second disadvantage is that if the reaction is carried to high conversion, the yield tends to fall off.

Substituting hydrogen acceptors such as cyclohexanone, which are less likely to undergo an aldol condensation, for the acetone may improve the aldehyde yield. Still, relatively high reaction temperatures are required when using ketones as hydrogen acceptors to carry out the oxidation to high conversion in a reasonable time. High temperatures would be a disadvantage with heat-sensitive aldehydes such as citral, as these are capable of self-condensation at high temperatures. In addition, other ketonic hydrogen acceptors present problems of availability or low equilibrium constants, the latter necessitating a large excess of hydrogen acceptor which causes difficulty in subsequent isolation of products.

Djerassi on page 230 points out: "Until recently aldehydes have been used only infrequently as hydrogen acceptors." Aldehydes are traditionally difficult products to make, being unstable and subject to side reactions. Use of an aldehyde as a reactant or hydrogen acceptor is subject to the same problems, being equally unstable and subject to side reactions. In the Oppenauer oxidation process, it is likely to undergo both aldol and Tischenko condensation reactions, with both itself and with the Oppenauer oxidation product.

A number of studies have been conducted by Adkins and others (for instance, Adkins et al., *J. Am. Chem. Soc.*, Vol. 71, pages 3622–3629) to determine the apparent oxidation potentials of various compounds (primarily ketones). Although it can be concluded that a high oxidation potential is desirable, a relatively low one (as pointed out by Djerassi on page 228) can be offset by using a large excess of hydrogen acceptor, and other factors such as rate of reaction and potential for side reactions may be more controlling. For instance, acetone has a relatively low oxidation potential but is inexpensive and can be used in large excess. Cyclohexanone on the other hand has a higher oxidation potential, but in comparative tests conducted with this compound, the oxidation of geraniol resulted in only 15% conversion to citral.

SUMMARY OF THE INVENTION

The present invention resides in the discovery that furfural unexpectedly constitutes a superior oxidizing agent or hydrogen acceptor for the conversion of 3-substituted and 3,3-disubstituted allyl alcohols to their corresponding aldehydes, and particularly for the conversion of geraniol and nerol to citral. The reaction of the present invention is carried out under mild Oppenauer oxidation conditions in the presence of an aluminum catalyst, and can be represented by the following equation:

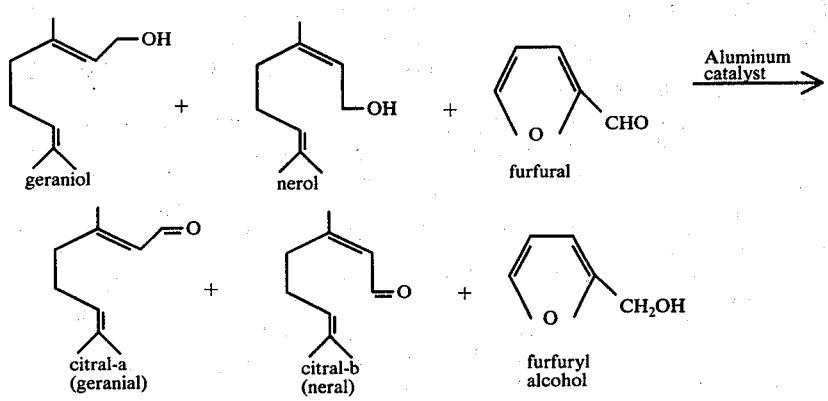

(1)

Under the mild reaction conditions, it was discovered that furfural does not undergo a Tischenko reaction as is common with many aldehydes. Moreover, furfural, having no alpha-protons, does not undergo an aldol condensation with the aldehyde product, for instance citral, as does acetone. Hence, the amount of aluminum catalyst required for the reaction is greatly reduced to catalytic quantities, eliminating the attendant mechanical and pollution problems, and reducing catalyst cost.

Surprisingly the reaction of furfural with substituted allyl alcohols such as nerol and geraniol has a high rate of reaction which permits it to be carried out under very mild conditions. This is important for such heat-sensitive compounds as citral. Specifically, at the mild conditions of the reaction of the present invention, citral, itself, undergoes no aldol self-condensation. Also, at the mild conditions of the present invention, no appreciable side reactions occur of the type resulting in such compounds as isocitrals and dimers.

The reaction of the present invention also has a fortuitous high equilibrium constant so that it results in high conversion and yields of citral without employing a large excess of furfural.

The citral reaction product is readily recovered and is sufficiently pure that it can be employed for most uses without purification. In this regard, furfuryl alcohol, which is also a product of the oxidation reaction, has a relatively low boiling point allowing its convenient separation from citral and recovery by distillation. It is a very valuable product priced about 10% above furfural and is useful in the making of certain resins, rendering the process of the present invention even more favorable economically.

A particular advantage of the present invention is that the citral reaction product is sufficiently pure that it can be used without purification for the production of pseudoionone. This is carried out in the presence of acetone in accordance with the following equation:

(2)

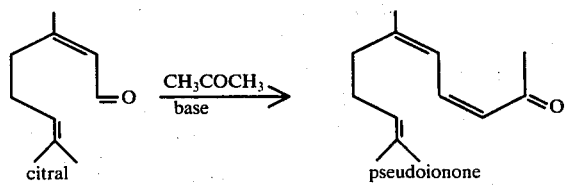

This reaction can be carried out with citral following separation from the other reaction products of equation (1), or alternatively can be carried out in a single pot process in which acetone and a base are added directly to the reaction mixture of equation (1).

Preferably, the reaction of equation (1) is carried out in the presence of furfural with a molar ratio of furfural to primary allylic alcohol of about 1:10 to about 10:1. A preferred range for nerol/geraniol is about 1:2 to about 3:1 which results in high yields of the desired products without excessive amounts of unreacted starting materials. The specific ratio selected, however, depends on the end products desired. In the production of pseudoionone, furfural also undergoes aldol condensation, so that it is desirable to employ a molar ratio of furfural to nerol/geraniol less than 1:1 in the order of about 3:4 to avoid the necessity of separating unreacted furfural prior to the conversion of citral to pseudoionone. On the other hand, if it is desired to recover citral, a relatively high molar ratio of furfural to nerol/geraniol in the order of 2:1, is employed to maximize the conversion.

Preferably, a catalytic amount of about 1-15 mol % (based on the weight of primary allylic alcohol charged) of an aluminum catalyst such as aluminum isopropoxide is employed, although this depends in part on the amount of water present in the reaction mixture.

For nerol/geraniol, the use of less than 2 mol % catalyst is possible if extreme care is taken with regard to the water content. Other factors dictating the amount of catalyst employed include rate of reaction desired, amount of coincidental acid present in the reaction mixture, and the amount of water or acid produced in the course of the reaction. As a general rule, about 5 mol % catalyst based on nerol/geraniol charged, gives optimum reacting conditions and efficiency; e.g., equilibrium in two to three hours at about 40° C.

Any aluminum alkoxide or aluminum aryloxide catalyst useful in an Oppenauer reaction, such as aluminum tert-butoxide [Al(t-OC$_4$H$_9$)$_3$], may be used. Aluminum isopropoxide is preferred as it offers a cost advantage and an advantage in availability, although some furfural is consumed by oxidation of the isopropoxide to acetone. In this regard, it is reported in the aforementioned *Organic Reactions*, Vol. VI, page 209 (Djerassi) and also in *Physical Organic Chemistry*, by Hine, that the true active catalyst in the oxidation is an aluminum alkoxide which is generated in situ, and thus is dependent upon the reactants and conditions. It is normally generated by the addition of aluminum isopropoxide, aluminum t-butoxide or aluminum phenoxide. It may also be generated in situ by addition of an alkyl aluminum compound such as triisobutylaluminum (Djerassi also lists a number of other suitable compounds). These compounds, although they are normally referred to as the catalyst, are merely the source of the aluminum alkoxide. Hence the choice of aluminum source is largely one of convenience. For the purpose of this application, the term "Oppenauer Oxidation Catalyst" shall be deemed to embrace all of the above compounds.

In its broadest aspect, the present invention relates to the Oppenauer oxidation of 3-substituted and 3,3-disubstituted allyl alcohols, as represented by the following formula:

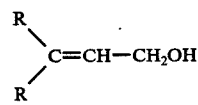

wherein the substitution is by either an aliphatic or aromatic group, or groups. In a preferred aspect of the present invention, the allyl alcohol may be disubstituted at the number 3 carbon atom with aliphatic groups. Representative compounds of this class are nerol/geraniol (supra); farnesol (3,7,11-trimethyl-2,6,10-dodecatrien-1-ol); prenol (3-methyl-2-buten-1-ol); and Vitamin A alcohol. In another class of compounds to which the present invention is directed; the allyl alcohol is substituted at the number 3 carbon atom with an aryl group. Representative of this class of compounds are cinnamyl alcohol ($C_6H_5CH=CHCH_2OH$); and polyhydroxyl aromatic carbinol compounds such as coniferyl alcohol [$p-HOC_6H_4CH=CHCH_2OH$].

Still a third class of compounds within the scope of the present invention are 3-substituted allyl alcohols wherein the substitution is by a single aliphatic group. A representative compound within the group is 2-hexen-1-ol.

Structures of representative alcohols are as follows:

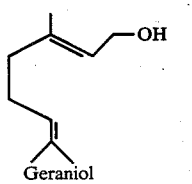
Geraniol

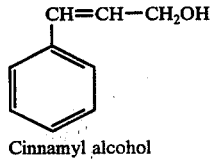
Cinnamyl alcohol

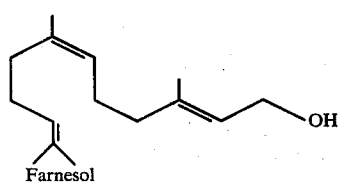
Farnesol

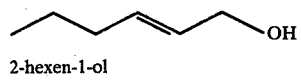
2-hexen-1-ol

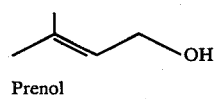
Prenol

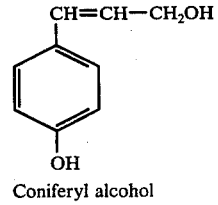
Coniferyl alcohol

The following examples illustrate the present invention and its practice, but should not be considered as limiting it. In this specification, all percentages are by weight, all parts are parts by weight, and all temperatures are in degrees Centigrade unless otherwise specified.

EXAMPLE 1

This example illustrates the oxidation of geraniol/nerol to citral using furfural as a hydrogen acceptor in accordance with the concepts of the present invention. A flask was charged with 1000 grams of redistilled geraniol/nerol (in a 60:40 ratio) and 475 grams of distilled furfural providing a molar ratio of furfural to nerol/geraniol of about 3:4. The mixture was heated to 35° C. and a solution of 50 grams of aluminum isopropoxide (5% by weight of nerol/geraniol charged) in 100 grams of toluene was added. The toluene may be omitted by predissolving the catalyst in the geraniol/nerol. Heating was discontinued, and the mixture was stirred at ambient temperature for about three (3) hours. The reaction was mildly exothermic. The mixture was analyzed by gas-liquid phase chromatography on a four-foot Carbowax column using tetradecane as an internal standard.

Table 1
Analysis of Reaction Product

| Compound | Weight Percent | Weight (grams) |
|---|---|---|
| Furfural | 1.06 | 17.3 |
| Furfuryl alcohol | 30.19 | 489.0 |
| Neral | 15.31 | 248.0 |
| Geranial | 24.70 | 400.1 |
| Nerol | 7.68 | 124.4 |
| Geraniol | 11.70 | 189.6 |
| Conversion of furfural | | 95.7% |
| Weight yield to furfuryl alcohol | | 105.2% |
| Conversion of geraniol/nerol | | 65.2% |
| Weight yield to citral | | 94.5% |

EXAMPLE 2

This example illustrates the course of the oxidation reaction as a function of time and shows that the oxidation of nerol/geraniol to citral may be carried out essentially to completion at equilibrium under very mild conditions employing furfural. The oxidation was carried out at room temperature and equilibrium was reacted in about five hours. The initial molar ratio of furfural to nerol/geraniol was approximately 5:3. Aluminum isopropoxide catalyst was employed, at ten percent (10%) weight level based on the weight of nerol/geraniol charged. The product analyses were made by gas-liquid phase chromatography using an internal standard.

Table II

| Time Hrs. | Conversion of Furfural (%) | Yield to Furfuryl Alc. (%) | Conversion of Nerol, etc. (%) | Yield to Citral (%) |
| --- | --- | --- | --- | --- |
| 0:10 | 9.56 | 99.97 | 17.59 | 100.02 |
| 1:11 | 44.22 | 99.78 | 65.72 | * |
| 2:26 | 60.60 | 100.73 | 85.19 | 98.67 |
| 4:38 | 63.03 | 99.09 | 90.46 | 97.08 |
| 5:40 | 63.20 | 101.54 | 91.44 | 96.87 |

It is apparent from the above data that even at room temperature conversions of about 85% of the nerol/geraniol to citral can be achieved in a relatively short time (2:26 hours) and that yields or recovery of citral of about 98% can be attained at that conversion. Even as the conversion is forced to about 90%, the drop in yield (percent recovery of citral produced) is slight. Tests indicate that yield losses over a 24-hour period are less than 5% at room temperature, with recoveries consistently in the 95–98% range. Major impurities are believed to be isocitrals. The purity of the resultant product, even following reaction to equilibrium, renders it suitable for use in the production of pseudoionone.

EXAMPLE 3

This example illustrates that the equilibrium of the oxidation of nerol using furfural is decidedly in favor of citral and furfuryl alcohol. This permits the reaction to be carried out conveniently to a high degree of conversion (e.g., 95% of either nerol or furfural without using a large excess of one reactant.

A number of tests were conducted at different molar ratios of furfural and nerol. The same oxidation conditions were employed in each test, namely, room temperature, 10% aluminum isopropoxide, and atmospheric pressure. The results are given in the following Table III:

Table III

| Molar Ratio Furfural:Nerol | Conversion of Furfural | Conversion of Nerol |
| --- | --- | --- |
| 2:4 | 97.9 | 44.6 |
| 3:4 | 95.2 | 68.0 |
| 4:4 | 87.2 | 79.4 |
| 5:4 | 81.2 | 89.6 |
| 6:4 | 71.0 | 93.0 |
| 7:4 | 60.4 | 94.2 |
| 8:4 | 53.8 | 97.6 |
| 10:4 | 44.2 | 98.2 |

The conversion of furfural is slightly higher than would be expected for the amount of nerol converted. The discrepency is due to some oxidation of isopropyl alcohol (from aluminum isopropoxide) to acetone. This reaction is much slower than the oxidation of nerol or geraniol and becomes apparent only when the nerol or geraniol oxidation approaches equilibrium.

EXAMPLE 4

A conversion of furfural to furfuryl alcohol of more than 90% is desirable if the crude citral product is to be converted directly to pseudoionone without purification of the citral. Furfuryl alcohol present and unreacted nerol and geraniol do not interfere with the reaction. A small amount of furfurylidene acetone is formed from the unreacted furfural during the pseudoionone reaction, but it does not interfere with the production and recovery of pseudoionone.

In this example, 390 grams of crude citral from Example 1 (i.e., the reaction product of Example 1 without purification) was caused to react with 1650 grams of 90% acetone using 100 ml. of 10% aqueous sodium hydroxide as the catalyst. Contained in the reaction mixture was only 1.06 weight percent furfural resulting from a 95.7% conversion of furfural to furfuryl alcohol from the reaction of equation (1). The pseudoionone reaction, illustrated by equation (2) above, was carried out by stirring at 40° to 43° C. for 2.5 hours. The product was neutralized with 20 ml. of acetic acid and acetone was stripped off at atmospheric pressure and a pot temperature of 100° C. The aluminum compounds were extracted with dilute sulfuric acid followed by saturated sodium carbonate. The product was then distilled at about 1 mm mercury pressure. Analyses showed a 105% weight yield of pseudoionone based on nerol/geraniol consumed, prior to the final distillation, and a 101% weight yield subsequent to the distillation.

Fractionation of furfuryl alcohol from pseudoionone should produce a theoretical yield of 113 grams of furfuryl alcohol (based on a 96% conversion of furfural). Analyses by gas-liquid phase chromatography showed 106.3 grams of furfuryl alcohol prior to final distillation and 95.1 grams after final distillation, for 82% recovered weight yield from furfural. Recovery in excess of 96% is feasible enhancing the economics of the process of this invention.

EXAMPLE 5

This example illustrates the principles of the invention in the Oppenauer oxidation of a hemiterpene alcohol, and in particular the oxidation of prenol (3-methyl-2-buten-1-ol) to prenal. Prenol is a commercially available product made by catalytic hydration of isoprene in glacial acetic acid to prenyl acetate which is then readily hydrolyzed to the alcohol. It can also be made directly from dimethylvinylcarbinol with dilute sulfuric acid. Prenal is a product useful as a synthetic flavor, having a desirable raspberry flavor.

The reaction of prenol to prenal may be represented by the following equation $$\text{Prenol} \diagup\!\!\diagdown\!\!\diagup\!\text{CH}_2\text{OH} \quad + \tag{3}$$

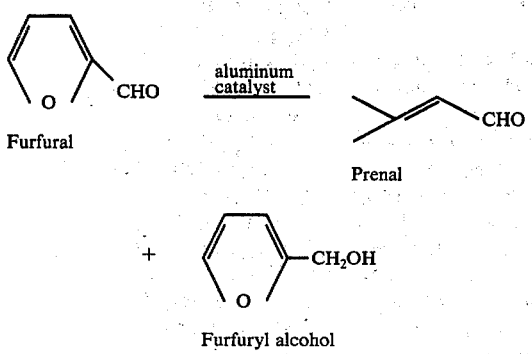

A flask was charged with 2.6 grams of aluminum isopropoxide and 21.5 grams of prenol and was stirred for fifteen minutes; 4.8 grams (2 equivalents) of furfural was then added giving mol ratios of 1:20 catalyst to prenol, and ~2:1 furfural to prenol. The mixture was then allowed to react with stirring at room temperature. Analyses by glpc showed about 70% conversion after 3 hours. Continuing the reaction overnight gave 98% conversion to prenal.

EXAMPLE 6

This example illustrates application of the concepts of the present invention in the oxidation of 2-hexen-1-ol.

A reactor was charged with five (5.0) grams of trans-2-hexen-1-ol, 5 grams of furfural and 2 ml of a 20% solution of aluminum isopropoxide in toluene. The mixture was allowed to react for 16 hours at room temperature. Analyses by gas-liquid phase chromatography showed 73% conversion of furfural to furfural alcohol and 71% conversion of hexanol to trans-2-hexenal. Only trace amounts of by-products totalling less than 2% of the crude product were observed.

EXAMPLE 7

In this example, farnesol is the substrate. A reactor was charged with 4.4 grams of farnesol (a mixture of 4 isomers of 3,7,11-trimethyl-2,6,10-dodecatrien-1-ol), 1.9 grams of furfural and 1 ml of a 20% solution of aluminum isopropoxide in toluene. The mixture was allowed to react for 14 hours at room temperature. Analyses by gas-liquid phase chromatography showed a 78% conversion of furfural to furfuryl alcohol and a comparable conversion of farnesol to farnesal. (Partial peak overlap of some isomers of farensol and farnesal prevented making a precise analysis of the conversion of farnesol to farnesal). The only by-products noted were about 5% of what were believed to be isofarnesals.

EXAMPLE 8

A reactor was charged with 2.6 grams of cinnamyl alcohol, 2.0 grams of furfural and 1.0 ml of a 20% solution of aluminum isopropoxide in toluene. The solution was allowed to react for 16 hours at room temperature. Analysis by gas-liquid chromatography showed 82% conversion of furfural to furfuryl alcohol and 85% conversion of cinnamyl alcohol to cinnamaldehyde. Less than about 2% by-products were detected.

EXAMPLE 9

This example illustrates the advantages of the invention using furfural as compared to the use of other hydrogen acceptors, namely cyclohexanone and benzaldehyde. The comparative reactions were carried out under the same conditions with equal equivalents of hydrogen acceptor, substrate and catalyst.

With benzaldehyde: A flask was charged with 3.1 grams of geraniol, 0.25 grams of aluminum isopropoxide and 2.1 grams (1 equivalent) of benzaldehyde and stirred for 16 hours at ambient temperature. Analysis by glpc showed only a 5% conversion of geraniol to citral.

With cyclohexanone: A flask was charged with 3.1 grams of geraniol, 0.25 grams of aluminum isopropoxide, and 1.9 grams (1 equivalent) of cyclohexanone and stirred for 16 hours at ambient temperature. Analysis by glpc showed only a 15% conversion to citral.

With furfural: A flask was charged with 3.1 grams of geraniol, 0.25 grams of aluminum isopropoxide, and 1.9 grams (1 equivalent) of furfural and stirred for 16 hours at ambient temperature. Analysis by glpc showed a 79% conversion of geraniol to citral.

EXAMPLE 10

In this example, comparative tests were conducted with furfural and isobutyraldehyde which has a higher oxidation potential under the same conditions. Two flasks were each charged with a solution of 0.5 grams of aluminum isopropoxide in 10 grams of geraniol. To one flask was added 1.5 equivalents of furfural and to the other 1.5 equivalents of isobutyraldehyde. Both flasks were allowed to react for 20 hours at ambient temperature. Analysis by glpc gave the following results:

| Hydrogen Acceptor | % of geraniol Consumed | % yield to Citral |
|---|---|---|
| Furfural | 94.0% | 98+% |
| Isobutyraldehyde | 78.2% | 88.1% |

EXAMPLE 11

This example illustrates the use of triisobutylaluminum to generate the aluminum alkoxide catalyst. A flask was charged with 80 grams of nerol and 10 ml of a 25% solution of triisobutylaluminum in toluene. To the solution was added 39 grams (0.75 equivalents) of furfural and the solution was allowed to react at ambient temperature for 18 hours. Analysis by glpc showed that 69% of the nerol had been consumed to give citral in 98+% yield.

What is claimed is:

1. In an Oppenauer oxidation for converting a 3-substituted or 3,3-disubstituted allyl alcohol having the following configuration

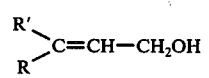

wherein R is an aliphatic or aromatic group and R' is hydrogen, an aliphatic or an aromatic group, into the corresponding olefin aldehyde, in the presence of an Oppenauer oxidation catalyst and hydrogen acceptor under mild temperature Oppenauer oxidation conditions, the improvement which comprises carrying out said oxidation in the presence of furfural as said hydrogen acceptor in a molar ratio of furfural to allyl alcohol of about 10:1–1:10 and forming a reaction product mixture containing the aldehyde corresponding to the allyl alcohol and as a by-product, furfuryl alcohol, said catalyst being employed in a catalytic amount.

2. The oxidation process of claim 1 wherein said Oppenauer reaction is carried out with a molar ratio of furfural to allyl alcohol in the range of 3:1 to 1:2.

3. The oxidation process of claim 1 wherein said allyl alcohol is disubstituted with aliphatic groups.

4. The oxidation process of claim 3 wherein said allyl alcohol is nerol/geraniol (3,7-dimethyl-2,6-octadien-1-ol), said reaction product mixture containing citral.

5. The oxidation process of claim 4 wherein the citral reaction product is caused to undergo an aldol condensation by reaction with acetone and base without intermediate purification and the aldol condensation product formed is pseudoionone.

6. The oxidation process of claim 5 wherein the molar ratio of furfural to nerol/geraniol being less than about 1:1.

7. The process of claim 3 wherein said allyl alcohol is prenol (3-methyl-2-buten-1-ol), oxidized to prenal.

8. The process of claim 3 wherein said allyl alcohol is farnesol (3,7,11-trimethyl-2,6,10-dodecatrien-1-ol), oxidized to farnesal.

9. The process of claim 1 wherein said allyl alcohol is mono-substituted with an aromatic group.

10. The process of claim 9 wherein said allyl alcohol is cinnamyl alcohol ($C_6H_5CH=CHCH_2OH$).

11. The process of claim 1 wherein said allyl alcohol is mono-substituted with an aliphatic group.

12. The process of claim 11 wherein said allyl alcohol is 2-hexen-1-ol.

13. In an Oppenauer oxidation for converting a 3-substituted or 3,3-disubstituted allyl alcohol selected from the group consisting of nerol/geraniol (3,7-dimethyl-2,6-octadien-1-ol), prenol (3-methyl-2-butene-1-ol), farnesol (3,7,11-trimethyl-2,6,10-dodecatrien-1-ol), cinnamyl alcohol ($C_6H_5CH=CHCH_2OH$) and 2-hexen-1-ol, into the corresponding olefin aldehyde in the presence of an Oppenauer oxidation catalyst and hydrogen acceptor under mild temperature Oppenauer oxidation conditions, the improvement which comprises carrying out said oxidation in the presence of furfural as said hydrogen acceptor in a molar ratio of furfural to alcohol of about 10:1–1:10 and forming a reaction product mixture containing the aldehyde corresponding to the allyl alcohol and as a by-product, furfuryl alcohol, said catalyst being employed in a catalytic amount.

* * * * *

UNITED STATES PATENT AND TRADEMARK OFFICE
CERTIFICATE OF CORRECTION

PATENT NO. : 4,055,601
DATED : October 25, 1977
INVENTOR(S) : William J. Ehmann

It is certified that error appears in the above-identified patent and that said Letters Patent are hereby corrected as shown below:

Col. 7, before line 17 and after the Table, insert --*Analysis not available.--; line 57, change "discrepency" to --discrepancy--. Col. 8, line 44, before "82%" insert --an--; line 61, after "following equation" insert --:--. Col. 9, line 34, change "furfural", second occurrence, to --furfuryl--. Col. 12, line 10, in claim 13, the portion of the compound reading "-2-butene-" should read -- -2-buten- --.

Signed and Sealed this

Fourth Day of April 1978

[SEAL]

Attest:

RUTH C. MASON
Attesting Officer

LUTRELLE F. PARKER
Acting Commissioner of Patents and Trademarks